(12) United States Patent
Yoon

(10) Patent No.: US 6,332,466 B1
(45) Date of Patent: Dec. 25, 2001

(54) OVARIAN CAPSULES AND METHODS OF SURGICAL CONTRACEPTION BY OVARIAN ENCAPSULATION

(76) Inventor: InBae Yoon, 2101 Highland Ridge Dr., Phoenix, MD (US) 21131

(*) Notice: Subject to any disclaimer, the term of this patent is extended or adjusted under 35 U.S.C. 154(b) by 0 days.

(21) Appl. No.: 09/110,451

(22) Filed: Jul. 7, 1998

Related U.S. Application Data

(60) Provisional application No. 60/051,941, filed on Jul. 8, 1997.

(51) Int. Cl.[7] ............................................. A61F 6/06
(52) U.S. Cl. ................................. 128/830; 128/832
(58) Field of Search ............................... 128/830–841

(56) References Cited

U.S. PATENT DOCUMENTS

| | | |
|---|---|---|
| 3,646,616 | 3/1972 | Keshin . |
| 4,050,448 | 9/1977 | Borgen . |
| 4,135,495 | 1/1979 | Borgen . |
| 4,267,839 | 5/1981 | Laufe et al. . |
| 4,869,268 | 9/1989 | Yoon . |
| 5,026,379 | 6/1991 | Yoon . |
| 5,217,473 | 6/1993 | Yoon . |
| 5,334,209 | 8/1994 | Yoon . |

Primary Examiner—Michael A. Brown
(74) Attorney, Agent, or Firm—Blank Rome Comisky & McCauley LLP

(57) ABSTRACT

An ovarian capsule includes a capsule body enclosing an interior for receiving an ovary and defining a selectively openable, selectively closeable access. The access, when open, forms a gap, space or opening in the ovarian capsule through which an ovary is introduced in the interior. When the access is closed, withdrawal of the ovary from the interior is prevented whereby the ovary is encapsulated by the ovarian capsule to prevent fertilization of ova released by the encapsulated ovary. A method of encapsulating an ovary in the body of a patient includes the steps of introducing an ovarian capsule in the abdominal cavity of the patient, opening the ovarian capsule to provide access to the interior thereof, positioning an ovary of the patient within the interior of the capsule and closing the ovarian capsule to encapsulate the ovary and prevent withdrawal of the ovary from the ovarian capsule.

54 Claims, 3 Drawing Sheets

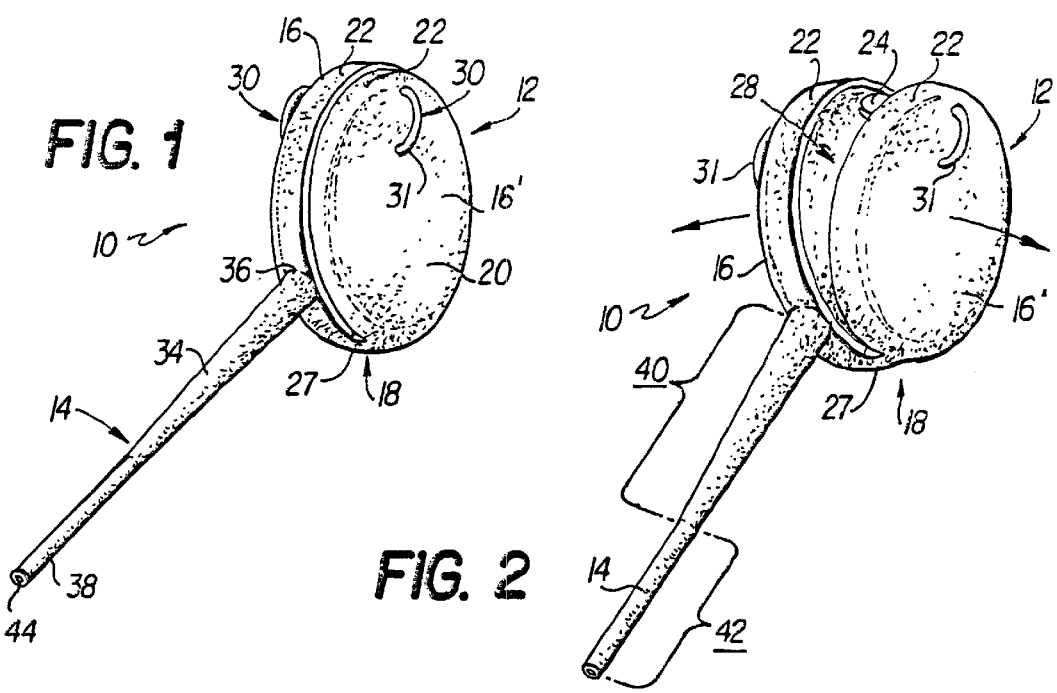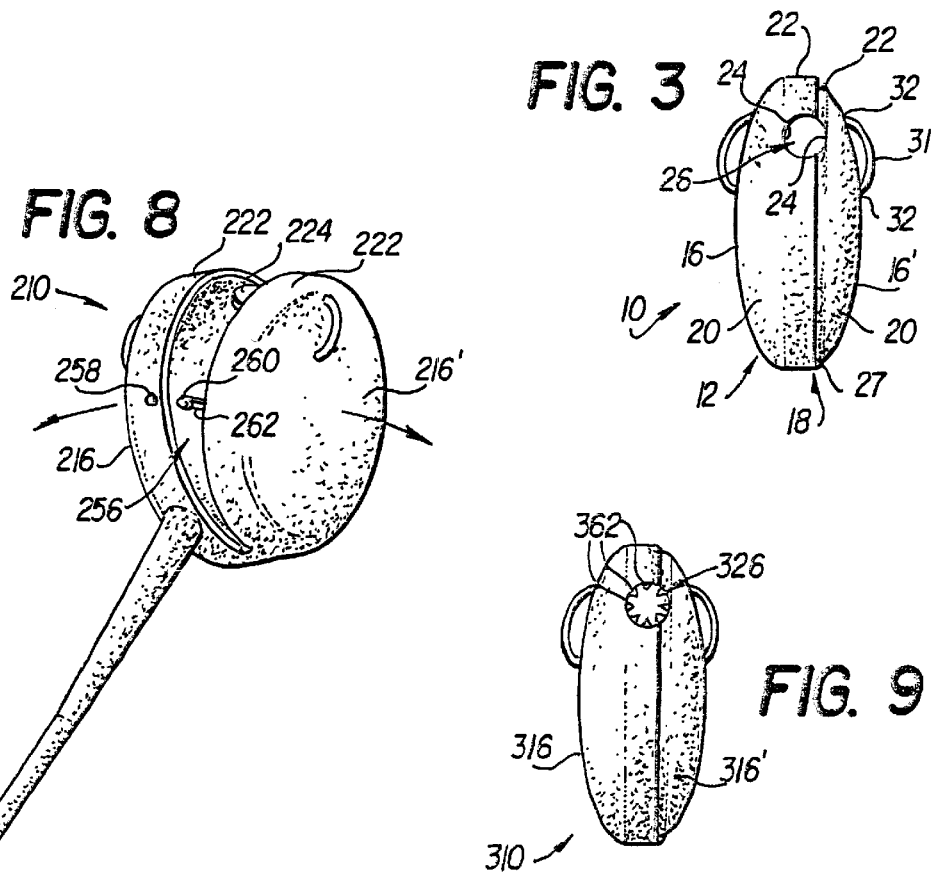

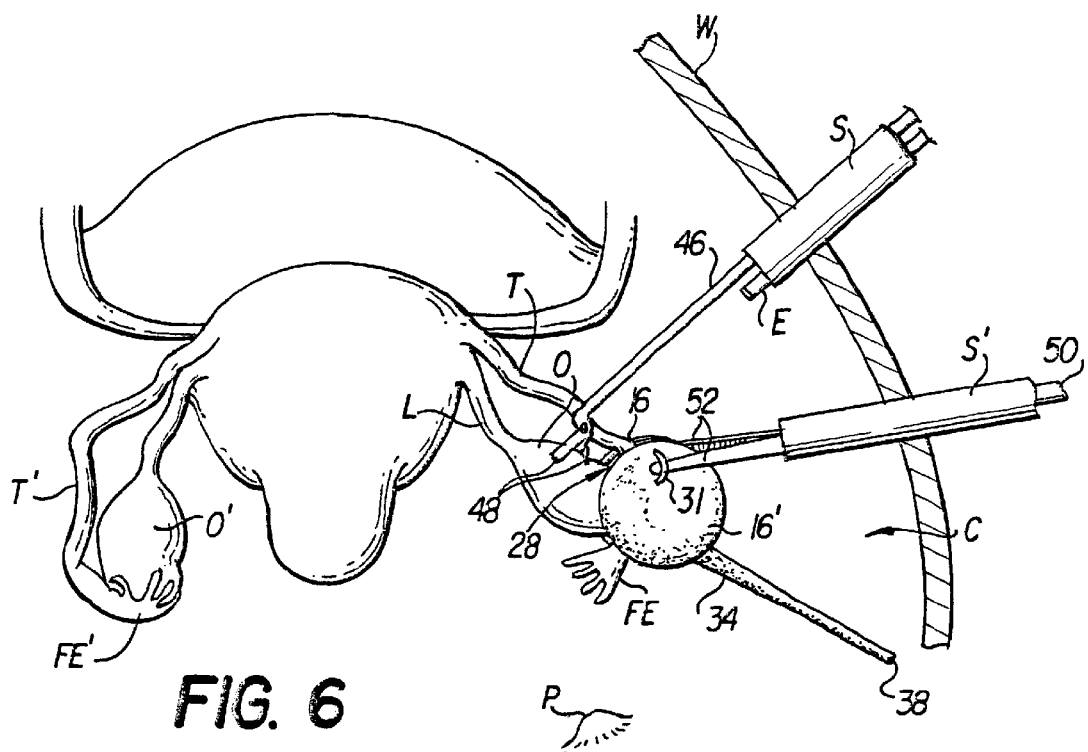
FIG. 6
FIG. 7
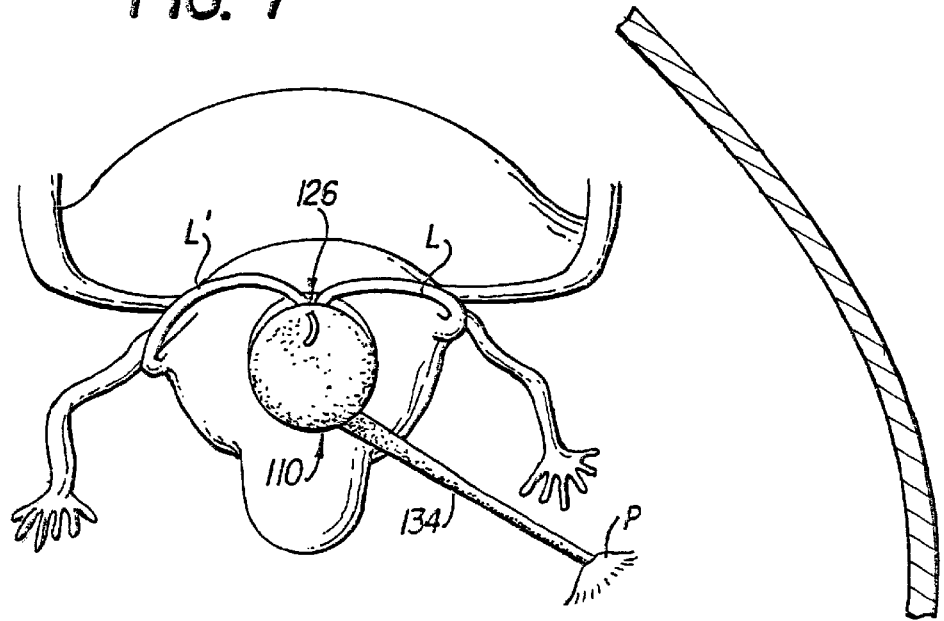

US 6,332,466 B1

OVARIAN CAPSULES AND METHODS OF SURGICAL CONTRACEPTION BY OVARIAN ENCAPSULATION

CROSS-REFERENCE TO RELATED PATENT APPLICATIONS

This application claims priority from provisional patent application Serial No. 60/051,941, filed Jul. 8, 1997, the disclosure of which is incorporated herein by reference.

BACKGROUND OF THE INVENTION

1. Field of the Invention

The present invention relates to surgical contraception of the female and, more particularly, to ovarian capsules and methods of performing both permanent and temporary, reversible surgical contraception by ovarian encapsulation.

2. Description of the Related Art

Female contraception is widely practiced to prevent pregnancy, either permanently or temporarily. Various contraceptive methods and devices are used to prevent pregnancy in females including, for example, natural family planning methods such as the rhythm method and coitus interruptus, spermicides, barrier devices such as the diaphragm, sponge, cap and condom, chemical or hormonal treatments such as birth control pills, intrauterine devices (IUDs) and tubal occluding devices and methods such as plugs, adhesives and tubal ligation. Many of the contraceptive devices and methods currently in use are user dependent and, therefore, have relatively high rates of failure due to non-use and/or improper use. In addition, some user dependent contraceptive methods and devices, such as rhythm and coitus interruptus, are inherently unreliable. User dependent methods and devices of female contraception have various drawbacks ranging from inconvenience to serious medical complications. Birth control pills, for instance, have been associated with adverse side effects including cardiovascular disease and, in particular, stroke.

Although non-user dependent methods and devices of female contraception have lower rates of failure, they also have many drawbacks. The IUD, for example, has been associated with pelvic inflammatory disease and undesired sterility. Surgical contraception such as tubal ligation has the drawback of being difficult to reverse to allow for future pregnancy due to blockage or damage of the Fallopian tubes incurred as part of the tubal ligation procedure. On the other hand, surgical contraception presents the advantages of being highly effective in preventing pregnancy and of eliminating the need for user intervention. Furthermore, surgical advances have greatly increased the safety and efficacy of surgical female contraceptive procedures. However, the various advantages of surgical contraception may be outweighed by the disadvantage of permanence or irreversibility where permanent contraception is not desired.

Accordingly, the need exists for surgical female contraception that is reliable and effective in preventing pregnancy but which is capable of being reversed if desired to allow for future pregnancy and which can be performed endoscopically with minimal invasiveness and trauma. The need also exists for surgical female contraception in addition to that presently available to increase the family planning and contraceptive options available to women.

SUMMARY OF THE INVENTION

Accordingly, it is a primary object of the present invention to overcome the aforesaid disadvantages of prior art devices and methods of female contraception.

Another object of the present invention is to encapsulate the ovaries of a female in the same ovarian capsule or in different ovarian capsules.

An additional object of the present invention is to prevent conception by encapsulating the ovaries of a female such that ova released by the ovaries cannot be fertilized.

It is also an object of the present invention to drain or release substances from an ovarian capsule in which an ovary is encapsulated.

The present invention has as another object to drain or release substances from an ovarian capsule into an anatomical space.

A further object of the present invention is to drain or release substances from an ovarian capsule into an anatomical space isolated from the abdominal cavity.

A still further object of the present invention is to drain or release substances from an ovarian capsule into a retroperitoneal space.

Yet another object of the present invention is to reverse contraception by ovarian encapsulation to allow for future pregnancy.

It is an additional object of the present invention to encapsulate the ovaries of a female endoscopically.

Some of the advantages of the present invention are that the ovarian capsules can be gently opened to receive one or more ovaries therein and can be gently closed to encapsulate the one or more ovaries therein without substantial force or pressure, the ovarian capsules can be made available in various sizes allowing a specific capsule to be selected in accordance with the size of the ovary or ovaries to be encapsulated therein, the ovarian capsules can be provided in a single size with the capsules being adjustable to accommodate one or more ovaries of various sizes, compression of the ovarian pedicles by the ovarian capsules is avoided, the ovarian capsules can be provided with engaging members for engagement with various instruments, such as forceps or graspers, used to hold the ovarian capsules and/or used to open and/or close the ovarian capsules in the patient's body, the ovarian capsules can be provided with various detent members for maintaining the ovarian capsules in a closed position following encapsulation of one or more ovaries therein, drains or outlets of varying lengths can extend from bodies of the ovarian capsules to drainage sites in the patient's body, the drains or outlets can be made of soft material atraumatic to tissue in the patient's body, the ovarian capsules can be applied to and/or withdrawn from one or more ovaries endoscopically, non-endoscopically or as a mini-lap procedure, and contraception via ovarian encapsulation according to the present invention can be permanent or temporary, reversible.

These and other objects, benefits and advantages are realized with the preset invention as characterized in an ovarian capsule including a capsule body enclosing an interior for receiving an ovary and defining a selectively openable and selectively closeable access. The access, when open, provides communication with the interior of the capsule body allowing an ovary to be introduced through the access into the interior of the ovarian capsule. When the access is closed, withdrawal of the ovary from the interior of the ovarian capsule is prevented such that the ovary is encapsulated by the ovarian capsule to prevent fertilization of ova released by the encapsulated ovary. The ovarian capsule has an opening through which the ovarian ligament or pedicle of the encapsulated ovary passes to extend externally of the ovarian capsule. The ovarian capsule can include an outlet or drain for draining substances such as fluid from the interior of the ovarian capsule, and such substances can be released at a selected drainage site in the patient's body. In one embodiment, the outlet or drain includes a tubular member extending from the capsule body and having a first end attached to the capsule body in communication with the interior thereof and an open, second end for being positioned at the drainage site. The open, second end of the tubular member can be buried within, beneath or behind anatomical tissue for drainage of substances in an anatomical pocket or space isolated from or not in communication with the abdominal cavity.

A method of encapsulating an ovary in the body of a patient includes the steps of introducing an ovarian capsule in the abdominal cavity of the patient, inserting an ovary of the patient through an access of the ovarian capsule and into the interior of the ovarian capsule and closing the access to encapsulate the ovary and prevent withdrawal of the ovary from the ovarian capsule. The ovarian capsule can be introduced in the abdominal cavity with the use of various instruments and can be opened and closed utilizing such instruments. Instruments used to open and close the ovarian capsule can be operated from externally of the abdominal cavity allowing ovarian encapsulation to be performed endoscopically with instruments introduced in the abdominal cavity through one or more small size ports or passages in the abdominal cavity wall.

Other objects and advantages of the present invention will become apparent from the following description of preferred embodiments taken in conjunction with the accompanying drawings, wherein like parts or parts providing like functions in each of the several figures are identified by the same reference characters.

BRIEF DESCRIPTION OF THE DRAWINGS

FIG. 1 is a perspective view of an ovarian capsule according to the present invention showing the ovarian capsule in a closed position.

FIG. 2 is a perspective view of an ovarian capsule according to the present invention showing the ovarian capsule in an open position.

FIG. 3 is an end view of the ovarian capsule in the closed position.

FIG. 6 is a superior view of the abdominal cavity illustrating withdrawal of the ovarian capsule of FIG. 4 from the ovary and removal of the drain or outlet from the retroperitoneal space.

FIG. 7 is a superior view of the abdominal cavity illustrating encapsulation of both ovaries of a patient in the same ovarian capsule.

FIG. 8 is a perspective view of an alternative embodiment of an ovarian capsule wherein the ovarian capsule has at least one detent member.

FIG. 9 is an end view of another embodiment of an ovarian capsule wherein the ovarian capsule has tissue gripping elements.

DESCRIPTION OF THE PREFERRED EMBODIMENTS

Figures 4, 5:
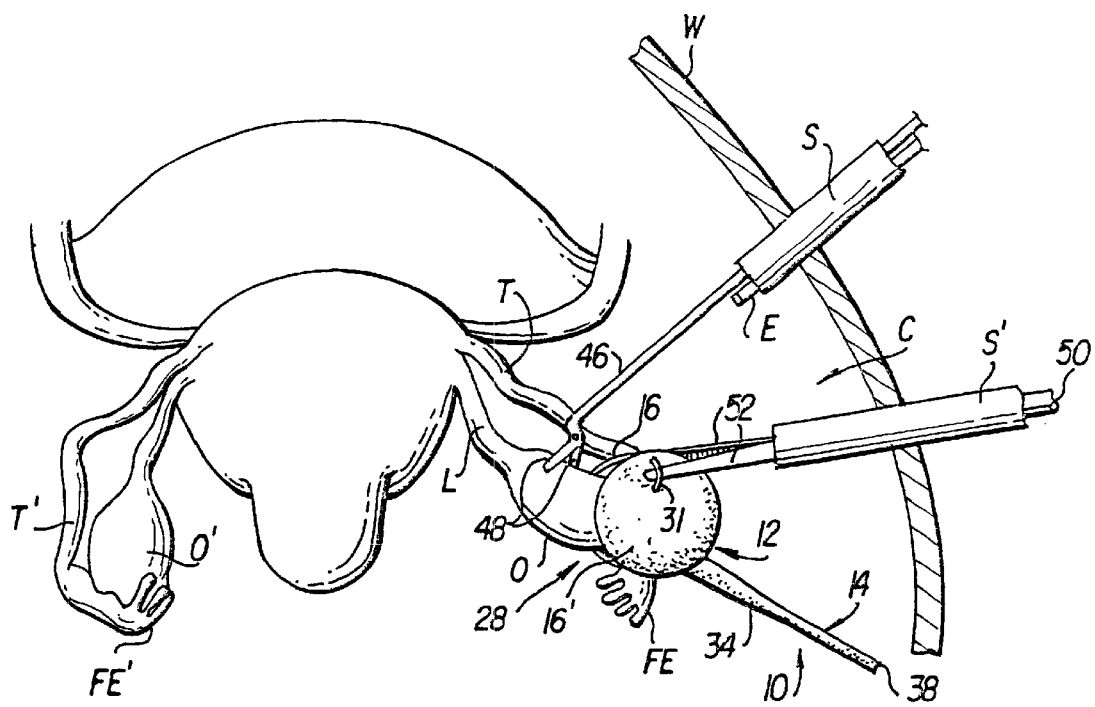
FIG. 4 is a superior view of the abdominal cavity showing the ovarian capsule in the open position with an ovary being positioned in the ovarian capsule in an endoscopic procedure of ovarian encapsulation.
FIG. 5 is a superior view of the abdominal cavity showing the ovarian capsule of FIG. 4 in the closed position encapsulating the ovary and the drain or outlet of the ovarian capsule buried in a retroperitoneal space.

An ovarian capsule 10 according to the present invention is illustrated in FIGS. 1–3 and includes a capsule body 12 and an outlet or drain 14 for the capsule body 12. The capsule body 12 is made up of first and second body portions 16 and 16' connected to one another by a connecting segment or tether 18. The body portions 16 and 16' each have a somewhat convex or dome-shaped wall 20 merging with a circumferential wall, rim or band 22. One of the body portions 16 is slightly larger than the other body portion 16' to allow the smaller body portion 16' to be disposed within the larger body portion 16 in a closed condition or position for the ovarian capsule 10 as shown in FIGS. 1 and 3. In the closed position, the circumferential wall 22 of the smaller body portion 16' is concentrically disposed within or inside of the circumferential wall 22 of the larger body portion 16, and the capsule body 12 encloses or circumscribes an interior having a size and configuration to receive an ovary. The capsule body 12 can be provided or made available in various sizes allowing an optimal size capsule to be selected in accordance with the size of an ovary to be encapsulated. For example, the capsule body 12 can be made available in diametric sizes such as 4 cm, 5 cm, 6 cm, etc. to receive different sized ovaries. The circumferential wall of the smaller body portion 16' is disposed within the circumferential wall of the larger body portion 16 with a close fit to form a seal or interface in the closed position preventing ova released by an ovary disposed in the interior from exiting or being released from the capsule through the seal or interface. The circumferential wall of the smaller body portion can be disposed within the circumferential wall of the larger body portion partly or entirely depending on the design of the ovarian capsule. In the case of capsule 10, the circumferential wall of body portion 16' is partly disposed within the circumferential wall of body portion 16 so as not to block or obstruct outlet 14.

A recess, cut-out or notch 24 is formed in each body portion 16 and 16' along the circumferential walls 22 thereof, and the recesses, cut-outs or notches 24 cooperate to form an opening or passage 26 in the capsule body 12 when the capsule is in the closed position. The opening 26 provides communication with the interior of the capsule body 12 from externally thereof when the capsule is in the closed position. The opening 26 is of a size and configuration to closely or snugly receive an ovarian ligament, i.e. the proper ligament or the ligament of the ovary, to extend or pass therethrough. Accordingly, an ovary can be disposed within the interior of the capsule body 12 for encapsulation thereby, with the ovarian ligament of the encapsulated ovary passing through the opening 26. The opening 26 is sufficiently close in size and configuration to the cross sectional size and configuration of the ovarian ligament or is slightly smaller in size than the cross sectional size of the ovarian ligament to prevent ova released by the encapsulated ovary from exiting the interior of the capsule body 12 through the opening 26. If desired, edges of body portions 16 and 16' cooperating to define or circumscribe the opening 26 can be provided with tissue gripping elements for gripping the ovarian ligament peripherally as explained further below. Exemplary tissue gripping elements suitable for use in the ovarian capsule 10 are disclosed in concurrently filed applications entitled Fimbrial End Capsules, Applicators Therefor and Methods of Surgical Female Contraception by Fimbrial End Encapsulation and Bilateral Fimbrial End Capsules, Applicators Therefor and Methods of Surgical Female Contraception by Bilateral Fimbrial End Encapsulation, the disclosures of which are incorporated herein by reference. In addition, the edges of body portions 16 and 16' defining opening 26 can be made resilient or elastic such that the opening 26 is expandable or stretchable/ contractible to receive and grip the ovarian ligament. Exemplary expandable and contractible variable size openings for a capsule are disclosed in the foregoing applications incorporated herein by reference. It is preferred that the ovarian capsule does not compress the ovarian ligament with undue pressure or force when the ovarian ligament passes through the opening 26 to avoid damage to or impairment of the ovarian ligament. It should be appreciated that the ovarian capsule 10 need not be provided with a pre-formed opening 26 in that, depending on the material from which the capsule is made, the capsule can resiliently or elastically deform around the ovarian ligament of an ovary disposed in the capsule interior.

The connecting segment or tether 18 connects the body portions 16 and 16' while allowing the body portions 16 and 16' to be moved away or separated from one another in an open condition or position for the capsule 10 as shown in FIG. 2. The connecting segment 18 for capsule 10 is in the nature of a hinge 27 and, in particular, a living hinge 27, located opposite the opening 26, such as being spaced 180 degrees from opening 26 along the circumferential walls 22. However, the opening 26 and the connecting segment 18 can be disposed at various locations on the capsule body 12. The connecting segment 18 is designed to bias the capsule 10 to the closed position while allowing the capsule 10 to be moved to the open position with minimal opening force or pressure. It should be appreciated that the connecting segment 18 can be formed integrally, unitarily with the capsule body 12 or separately therefrom as a discrete element or part. In addition or alternative to the closing bias provided by connecting segment 18, the capsule 10 can be provided with one or more releasable detent members for holding or securing the capsule in the closed position and for being released to allow the capsule to be moved to the open position.

The capsule 10 is moved from the closed position to the open position by manually moving the body portions 16 and 16' away from one another in the direction of the arrows in FIG. 2 causing the body portions 16 and 16' to pivot or rotate about connecting segment 18. In the open position, the smaller body portion 16' is withdrawn from the larger body portion 16, partly or entirely, creating a gap, space, access or opening 28 between the body portions 16 and 16' through which an ovary can be positioned in the interior. When the manual opening force on the capsule 10 is released, the capsule 10 returns to the closed position due to the closing bias thusly encapsulating the ovary in the interior, the body portions 16 and 16' gently snapping together in the manner of a snap fit. It should be appreciated that the capsule 10 need not be biased to the closed position in which case the capsule 10 can be manually moved from the open position to the closed position with a closing or compressive force sufficient to move the body portions 16 and 16' toward one another. Where the capsule 10 is biased to the closed position, the capsule 10 can, in addition, be manually moved from the open position to the closed position. The capsule 10 is preferably designed to be moved from the open position to the closed position with minimal closing force.

Engaging members 30 are provided on the capsule 10 to facilitate engagement of the capsule 10 with an instrument used to manually open and/or close the capsule. The engaging members 30 are provided on the body portions 16 and 16', respectively, and are in the nature of curved handles 31. As shown in FIG. 3, each handle 31 has opposing ends 32 secured to the corresponding body portion, and a space is formed between each handle 31 and its corresponding body portion. The engaging members 30 can be formed integrally, unitarily with the capsule 10 as one piece or separately therefrom as discrete elements or parts. The engaging members 30 can be provided at various locations on the capsule 10.

The outlet or drain 14 includes an elongate, hollow or tubular member 34 having a first end 36 attached to the capsule body 12, an open, second, free end 38 and a length between the first and second ends. The tubular member 34 has a first length segment 40 of non-uniform or decreasing diameter or circumference extending from capsule body 12 and a second length segment 42 of uniform or constant diameter or circumference extending from the first length segment. A lumen, passage or channel 44 of the tubular member 34 extends between the first and second ends and communicates with the interior of capsule body 12 at the first end 36. The tubular member 34 can have various lengths to permit the second end 38 to be positioned at a desired drainage site within a patient's body as discussed further below, and the length of the tubular member 34 can be selected in accordance with the location of the desired drainage site. The tubular member 34 can be attached to the capsule body 12 at various locations on the capsule body, and the tubular member 34 can extend from the capsule body at various angles therewith. The tubular member 34 can be designed to bend or flex and/or the tubular member 34 can be designed to pivot, rotate or bend about its first end 36. The drain 14 can be designed as a self-opening, self-closing drain as disclosed for the outlets or drains in the applications incorporated herein by reference and entitled, respectively, Fimbrial End Capsules, Applicators Therefor and Methods of Surgical Female Contraception By Fimbrial End Encapsulation and Bilateral Fimbrial End Capsules, Applicators Therefor and Methods of Surgical Female Contraception By Bilateral Fimbrial End Encapsulation. The drain 14 can be designed to open in response to a predetermined pressure in the capsule interior and can be designed to close upon relief of such pressure as disclosed in the applications incorporated herein by reference.

The capsule body 12 is preferably made of a membrane of medical grade, non-tissue reactive impervious, non-toxic, non-carcinogenic, non-clotting, smooth, preferably slippery material such as rubber, silastic, goretex or tecoflex. The material of the capsule body 12 can be translucent or transparent to permit visualization of the interior of the capsule body from externally thereof. The material of the capsule body can carry or be impregnated with various medicaments such as anti-adhesives, heparin powder adhesives, antibiotics, coagulants, anticoagulants, anesthetics and hormonal substances. The material of the capsule body 12 can itself have sufficient rigidity to maintain the desired shape or configuration. Alternatively or in addition to the rigidity of the material of the capsule body, the capsule body can have various shape maintaining members or elements disposed on or in the material thereon. Exemplary shape maintaining members or elements for a capsule are disclosed in the application entitled Fimbrial End Capsules, Applicators Therefor and Methods of Surgical Female Contraception By Fimbrial End Encapsulation incorporated herein by reference. The capsule body can be made of stretchable or elastic materials; and, where the capsule body is stretchable or elastic, the capsule can be provided in a single size with the capsule being adjustable, expandable or stretchable to accommodate ovaries of various sizes. The capsule body 12 can be integrally, unitarily formed as one piece in that the body portions 16 and 16' need not be formed as separate parts. In addition, the capsule body 12 need not comprise pivotal or movable body portions in that the capsule body can be formed as one piece with a selectively openable, selectively closeable access, such as a slot, flap or other access opening.

The connecting segment, the engaging members and/or the drain can be made of the same material as the capsule body 12 or can be made of materials different than the capsule body. It is preferred that the drain 14 be made of soft material atraumatic to anatomical tissue. The connecting segment, the engaging members and/or the drain can be made integrally, unitarily as one piece with the capsule body or can be made as a separate part or parts. It is preferred that the capsule 10 be without any sharp corners or edges so as not to damage or irritate anatomical tissue in the patient's body. Ovarian encapsulation according to the present invention can be performed endoscopically, non-endoscopically, as an open procedure or as a mini-lap procedure. FIGS. 4–6 illustrate a multi-port endoscopic procedure of surgical female contraception by ovarian encapsulation according to the present invention. In an endoscopic procedure of surgical contraception by ovarian encapsulation, one or more narrow or small size ports or passages in the patient's body are utilized to access the abdominal cavity, the one or more ports or passages providing communication with the abdominal cavity from externally thereon. The size of the one or more ports or passages is preferably no larger than necessary to receive or accommodate instruments to be used during the procedure, one such instrument including a remote visualization apparatus such as an endoscope, for visualizing the abdominal cavity from externally thereof. Preferably, the diametric or cross sectional size or the one or more ports is minimized to allow the ovarian encapsulation procedure to be performed endoscopically utilizing local anesthesia and non-hospital sites. The number of ports will be dependent on whether the instruments to be utilized are to be introduced through a single port or through multiple ports. The ports can be artificially created openings or incisions or natural anatomical openings or passages.

The one or more ports can be established conventionally in an endoscopic procedure by penetrating the wall of the abdominal cavity and introducing insufflation gas in the abdominal cavity to create a pneumoperitoneum. Typically, a small diameter hollow needle is utilized to penetrate or puncture the abdominal cavity wall and to introduce gas, such as carbon dioxide or nitrous oxide, into the abdominal cavity to create the pneumoperitoneum, thusly expanding the abdominal cavity for visualization and access. The needle is withdrawn and a larger diameter penetrating instrument, typically including a penetrating member or trocar disposed in a portal sleeve, is introduced through the puncture formed by the needle to introduce a distal end of the portal sleeve in the abdominal cavity. The trocar is withdrawn from the portal sleeve leaving the portal sleeve in place to extend through the cavity wall to provide a port or passage therethrough establishing communication with the abdominal cavity from externally thereof. Instruments can be introduced in the abdominal cavity through the port or passage of the portal sleeve; and, where multiple portal sleeves are installed, instruments can be introduced through any and all of the portal sleeves.

The various instruments introduced through the one or more ports have their distal ends positioned in the abdominal cavity and their proximal ends disposed externally of the abdominal cavity allowing the instruments to be manipulated, operated and/or maneuvered via their proximal ends under visualization provided externally of the abdominal cavity by the endoscope. If desired, a uterine grasper or manipulator (not shown) can be introduced vaginally or through one of the one or more ports for holding and/or manipulating the uterus during the ovarian encapsulation procedure.

FIG. 4 illustrates a distal end of a remote visualization apparatus E, such as an endoscope or laparoscope, introduced in the abdominal cavity C of a patient through a passage of a first passage defining member or portal sleeve S extending through abdominal cavity wall W with a proximal end of the endoscope E maintained externally of the cavity C. A distal end of an offset forceps or grasper 46 is introduced in the abdominal cavity C through the sleeve S, the forceps 46 being introduced through the same passage as endoscope E or through the first passage defining member or a different passage. In the case of forceps 46, the forceps 46 are introduced through the first passage defining member or sleeve S. The distal end of forceps 46 includes grasping members 48 operable via a proximal end (not shown) of the forceps 46 disposed externally of the abdominal cavity C. The grasping members 48 are operable to pick up and grasp an ovary O for positioning in a first ovarian capsule 10. A distal end of a second forceps or grasper 50 is introduced in the abdominal cavity C through a second portal sleeve S' extending through abdominal cavity wall W. Grasping members 52 at the distal end of forceps 50 carry capsule 10 with the grasping members 52 extending through the spaces, respectively, between the handles 31 and the body portions 16 and 16'. The forceps 50 is utilized to introduce the ovarian capsule 10 in the abdominal cavity through sleeve S', the capsule 10 collapsing or deforming to fit through the sleeve S'. The grasping members 52 are movable, from a proximal end (not shown) of forceps 50 disposed externally of the abdominal cavity C, inwardly toward one another and outwardly away from one another to move capsule 10 between the open and closed positions. The abdominal cavity C and the instruments and operative procedures therein are visualized externally of the abdominal cavity with the endoscope E. It should be appreciated that the ovarian capsule 10, the endoscope E, the forceps 46 and the forceps 50 can be introduced through the same portal sleeve as would occur in a single port procedure.

Initially, the ovaries O and O' of the patient are dissected from surrounding anatomical tissue including the corresponding fimbrial ends FE and FE' of the Fallopian tubes T and T', respectively, and the corresponding broad ligaments, respectively, such dissection being accomplished with the forceps 46 and/or forceps 50 or with other instruments introduced through portal sleeves S or S'. In order to accomplish dissection or cutting with forceps 46 and/or forceps 50, the grasping members 48 and/or the grasping members 50 can be designed to cut, sever or dissect anatomical tissue, mechanically and/or utilizing energy such as electricity for electric cutting. The ovaries O and O' can be dissected from surrounding anatomical tissue prior to introduction of capsule 10 in the abdominal cavity C. In FIG. 4, the ovary O is shown dissected from surrounding anatomical tissue.

Once the ovary O has been dissected from surrounding anatomical tissue, the grasping members 48 are utilized to pick up and grasp the ovary O as shown in FIG. 4. The grasping members 52, which have been introduced in the abdominal cavity C carrying the capsule 10 in the closed position, are moved outwardly away from one another to move the capsule 10 from the closed position to the open position. Accordingly, the access 28 is created between the body portions 16 and 16'; and, as shown in FIG. 4, the forceps 50 and/or the forceps 46 are manipulated to introduce or place the ovary O in the interior of the capsule body 12 via the access 28. The entire ovary O is positioned in the interior of the capsule body 12 via the access 28 and the ovarian ligament L for ovary O is aligned with the recesses 24.

Upon the ovary O being properly positioned in the interior of the capsule body 12, the grasping members 52 are released or are moved inwardly toward one another causing movement of capsule 10 from the open position to the closed position. The body portions 16 and 16' will snap or fit together thusly closing the access 28. The ovary O will then be encapsulated in the ovarian capsule 10 with the ovarian ligament L passing through the opening 26 as shown in FIG. 5, wherein the forceps 46 have been disengaged or released from the ovary O. The grasping members 52 are utilized to pick up and grasp the tubular member 34, and the forceps 50 is manipulated from externally of the abdominal cavity C to position the second end 38 of tubular member 34 at a drainage site in the patient's body. In the procedure shown in FIG. 5, the drainage site is the retroperitoneal space such that the tubular member 34 extends or passes through the peritoneum P with the end 38 positioned behind or in back of the peritoneum P. Fluids and substances that may collect within the interior of the capsule body 12 are drained or released therefrom into the retroperitoneal space behind the peritoneum P, such fluids being transported by tubular member 34. The drainage site of FIG. 5 does not communicate with the abdominal cavity C since the tubular member 34 passes through an opening in the peritoneum P no larger than necessary to accommodate the tubular member 34. Accordingly, fluids drained from capsule 10 are isolated from the abdominal cavity.

The foregoing procedure is repeated for ovary O' utilizing a second, different ovarian capsule. The second end of the outlet or drain for the second ovarian capsule is positioned at a drainage site in the abdominal cavity, which can be the same drainage site as or a different drainage site from the drainage site of the first ovarian capsule. However, it should be appreciated that both ovaries O and O' can be encapsulated in the same ovarian capsule in which case both ovarian ligaments L and L' can pass through the opening 26. It should be appreciated that the opening 26 can be made larger where both ovarian ligaments are to pass therethrough. It should be further appreciated that the ovarian capsule can be provided with two openings 26 for passage therethrough of ovarian ligaments L and L', respectively, and that the openings 26 can be located at various places on the ovarian capsule. Following encapsulation of both ovaries O an O', the forceps, endoscope and sleeves are withdrawn from the abdominal cavity. With the ovaries O and O' encapsulated by the same ovarian capsule or different ovarian capsules, conception and pregnancy cannot occur since ova released by the ovaries O and O' cannot be fertilized and cannot be received by the Fallopian tubes T and T', respectively. Surgical contraception by ovarian encapsulation can be reversed to allow for future pregnancy. Ovarian encapsulation can be surgically reversed in an open or non-endoscopic procedure, an endoscopic procedure or in a mini-lap procedure. FIG. 6 illustrates an endoscopic procedure of reversal of ovarian encapsulation wherein visualization is provided externally of the abdominal cavity C by endoscope E introduced in abdominal cavity C through sleeve S. Grasping members 48 of forceps 46, which is introduced in the abdominal cavity C through sleeve S, is utilized to hold ovary O. Grasping members 52 of forceps 50, which is introduced in the abdominal cavity C through sleeve S' is utilized to grasp tubular member 34 and withdraw the end 38 from the peritoneum P to withdraw the drain from the retroperitoneal space, i.e. the drainage site. Following release, removal or withdrawal of end 38 from the drainage site, the grasping members 52 are used to grasp or engage ovarian capsule 10 via handles 31. The grasping members 52 are moved outwardly away from one another to move the capsule 10 from the closed position to the open position, the grasping members 52 being operated externally of the abdominal cavity C. Accordingly, the body portions 16 and 16' are moved away from one another thusly creating or forming access 28. The forceps 50 and/or the forceps 46 are moved or manipulated as necessary, with the capsule 10 held in the open position by grasping members 52, to withdraw the ovary O from the capsule 10, the ovary O passing through the access 28 between the body portions 16 and 16'. The capsule 10 and forceps 50 are removed from the abdominal cavity C through the sleeve S', the capsule 10 collapsing or deforming as necessary to fit through the sleeve S'.

FIG. 7 illustrates ovarian encapsulation wherein both ovaries of a patient are encapsulated in the same ovarian capsule 110. Ovarian capsule 110 is similar to ovarian capsule 10 except that the opening 126 of ovarian capsule 110 is designed to receive both ovarian ligaments L and L' therethrough. The ovarian capsule 110 has the second end of tubular member 134 buried in the retroperitoneal space being the peritoneum P.

An alternative ovarian capsule according to the present invention is illustrated at 210 in FIG. 8. Ovarian capsule 210 is similar to ovarian capsule 10 except that ovarian capsule 210 includes at least one releasable detent for locking the ovarian capsule 210 in the closed position. The detent includes a detent member 256 on body portion 216' and an aperture 258 in body portion 216 for receiving a locking protrusion 260 of the detent member 256 when the capsule 210 is in the closed position. Detent member 256 includes a flexible or resilient finger 262 extending from the circumferential wall 222 of body portion 216' in the direction of body portion 216 and the locking protrusion 260 at a free end of the finger 262. The locking protrusion 260 is carried or formed on an outer surface of the finger 262. The finger 262 is resilient to deflect, pivot or move inwardly in the direction of the center of the capsule body to enter the interior of body portion 216 when the capsule 210 is moved from the open position shown in FIG. 8 to the closed position. The aperture 258 is formed in the circumferential wall 222 of body portion 216 to receive the locking protrusion 260 when the capsule is moved to the closed position, the locking protrusion 260 springing into the aperture 258. With the locking protrusion 260 disposed in the aperture 258, the detent will be in a locked position with the capsule 210 locked in the closed position. In the locked position, the locking protrusion will protrude slightly externally of the circumferential wall 222 of body portion 216. The detent for capsule 210 is spaced approximately 90 degrees from recesses 224; and, preferably, two detents are provided on ovarian capsule 210 spaced 180 degrees from one another.

In order to release the detent of capsule 210 to unlock the capsule 210 for movement to the open position, the locking protrusion 258 is compressed or moved inwardly in the direction of the center of the capsule body to disengage or release the locking protrusion 258 from the aperture 258 as permitted due to flexing of finger 262 inwardly. Various instruments can be utilized to unlock or release the detent. For example, the grasping members 52 of forceps 50 can be utilized to compress the capsule body between the grasping members at the location of the locking protrusion; and, where two detents are provided 180 degrees from one another, the grasping members can be used to unlock both detents simultaneously.

FIG. 9 illustrates at 310 an alternative ovarian capsule having tissue gripping elements for gripping an ovarian ligament. Ovarian capsule 310 is similar to ovarian capsule 210 except that the edges of body portions 316 and 316' defining opening 326 are provided with tissue gripping elements 362 such that the tissue gripping elements 362 extend along or around the opening 326 and protrude into the opening 326. The tissue gripping elements are of the type disclosed in the applications incorporated herein by reference and entitled Fimbrial End Capsules, Applicators Therefor and Methods of Surgical Female Contraception By Fimbrial End Encapsulation and Bilateral Fimbrial End Capsules, Applicators Therefor and Methods of Surgical Female Contraception By Bilateral Fimbrial End Encapsulation.

The ovarian capsules according to the present invention can be used for permanent or temporary, reversible contraception. The ovarian capsules can be applied to and/or removed from the ovaries as open or non-endoscopic surgery, endoscopically or as mini-lap procedures. The ovarian capsules are atraumatic to the ovaries and surrounding anatomical tissue or organ structure. The ovarian capsules can be opened and closed with minimal force; and, when closed, the ovarian capsules exert minimal pressure on the ovaries. Various instruments can be used to introduce the ovarian capsules in the patient's body, to grasp the ovaries and/or to apply the capsules to the ovaries. Such instruments can include various forceps or graspers including offset forceps or graspers. Exemplary forceps or graspers are disclosed in applications entitled Instrument Assemblies For Performing Anatomical Tissue Ligation filed May 1, 1997, Surgical Instrument with Rotatably Mounted Offset End Effector and Method of Using the Same filed May 1, 1997, Surgical Instrument with Multiple Rotatably Mounted Offset End Effectors and Method of Using the Same filed May 1, 1997, Suturing Instrument with Rotatably Mounted Offset Needle Holder and Method of Using the Same filed May 1,1997, Suturing Instrument with Multiple Rotatably Mounted Offset Needle Holders and Method of Using the Same filed May 1, 1997, and concurrently filed applications entitled Instruments, Instrument Assemblies and Methods For Surgical Female Contraception by Fimbrial End Burying, Fimbrial End Capsules, Applicators Therefor and Methods of Surgical Female Contraception By Fimbrial End Encapsulation, and Bilateral Fimbrial End Capsules, Applicators Therefor and Methods of Surgical Female Contraception By Bilateral Fimbrial End Encapsulation, the disclosures of all the latter applications being incorporated herein by reference. The ovarian capsules can be carried by and applied to the ovaries by an applicator as disclosed in the applications incorporated herein by reference and entitled Fimbrial End Capsules, Applicators Therefor and Methods of Surgical Female Contraception By Fimbrial End Encapsulation and Bilateral Fimbrial End Capsules, Applicators Therefor and Methods of Surgical Female Contraception By Bilateral Fimbrial End Encapsulation. Depending on the instruments used to open and close the capsules, the capsules can be provided with various engaging members or structure to facilitate engagement or holding of the capsules by the instruments. The capsules can be provided with various outlets or drains as disclosed herein and in the applications incorporated herein by reference.

Substances can be released from the ovarian capsules in the patients body including the abdominal cavity as well as anatomical spaces or pockets isolated from and not in communication with the abdominal cavity. Exemplary drainage sites include the retroperitoneal space and the broad ligament space. Where the drainage sites are anatomical spaces or pockets, such spaces or pockets can be artificially created or can be natural anatomical spaces or pockets. Anatomical spaces or pockets can be artificially created in various ways utilizing various instruments. Instruments and methods for creating anatomical spaces or pockets are disclosed in the application entitled Instruments, Instrument Assemblies and Methods of Surgical Female Contraception By Fimbrial End Burying, incorporated herein by reference. The ovarian capsules can include the various drains or outlets disclosed in the applications entitled Fimbrial End Capsules, Applicators Therefor and Methods of Surgical Female Contraception By Fimbrial End Encapsulation and Bilateral Fimbrial End Capsules, Applicators Therefor and Methods of Surgical Female Contraception By Bilateral Fimbrial End Encapsulation incorporated herein by reference, and the drains or outlets of the ovarian capsules can release substances at the various drainage sites as disclosed in the latter applications.

One or both of the ovaries, subsequent to being encapsulated, can be buried in an anatomical pocket as described for the fimbrial end capsules in the applications incorporated herein by reference and entitled Fimbrial End Capsules, Applicators Therefor and Methods of Surgical Female Contraception By Fimbrial End Encapsulation and Bilateral Fimbrial End Capsules, Applicators Therefor and Methods of Surgical Female Contraception By Bilateral Fimbrial End Encapsulation. Both ovaries of a patient can be encapsulated in the same ovarian capsule, which can be formed as a bilateral ovarian capsule as disclosed for a bilateral fimbrial end capsule in the application incorporated herein by reference and entitled Bilateral Fimbrial End Capsules, Applicators Therefor and Methods of Surgical Female Contraception By Bilateral Fimbrial End Encapsulation.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A capsule for encapsulating an ovary in the body of a patient comprising
   a membrane configured to enclose an interior for receiving an ovary and defining a selectively openable, selectively closeable access, said access when open forming a gap through which an ovary is introduced in said interior, said access when closed preventing withdrawal of the ovary from said interior whereby the ovary is encapsulated by said capsule; and
   an opening in said membrane through which the ovarian ligament of an ovary encapsulated by said capsule passes.

2. A capsule as recited in claim 1 wherein said membrane includes an outlet through which fluids are drained from said interior.

3. A capsule as recited in claim 2 wherein said outlet includes a tubular member extending from said membrane.

4. A capsule as recited in claim 3 wherein said membrane is stretchable.

5. A capsule as recited in claim 4 wherein said membrane is made of rubber.

6. A capsule as recited in claim 3 wherein said membrane contains a medicament.

7. A capsule as recited in claim 2 wherein said access is biased to a closed position, is movable to an open position in response to an opening force applied to said membrane and returns automatically to said closed position upon release of the opening.

8. A capsule for encapsulating an ovary in the body of a patient comprising
   a capsule body including first and second portions movable from a closed position wherein said first and second portion enclose an interior for receiving an ovary to an open position wherein an access is defined between said first and second portions through which an ovary is positioned in said interior, said first and second portions being movable from said open position to said closed position after positioning of an ovary in said interior to close said access and prevent withdrawal of the ovary from said capsule body; and
   an opening in said capsule body for receiving the ovarian ligament of the ovary to extend therethrough whereby the ovary is encapsulated by said capsule body.

9. A capsule as recited in claim 8 wherein said first and second portions are connected to one another.

10. A capsule as recited in claim 9 wherein said first and second portions are pivotally connected to one another for pivotal movement between said closed and open positions.

11. A capsule as recited in claim 10 wherein said capsule body further includes a connecting segment connecting said first and second portions and said first and second portions are pivotable about said connecting segment.

12. A capsule as recited in claim 11 wherein said first and second portions are pivotable away from one another for movement from said closed position to said open position and are pivotable toward one another for movement from said open portion to said closed position.

13. A capsule as recited in claim 12 wherein said connecting segment is a hinge.

14. A capsule as recited in claim 13 wherein one of said first and second portions is disposed within the other of said first and second portions in said closed position.

15. A capsule as recited in claim 8 wherein said opening is defined by a first recess in said first portion and a second recess in said second portion, said first and second recesses cooperating to form said opening in said closed position.

16. A capsule as recited in claim 15 wherein said opening has a configuration and size to snugly receive the ovarian ligament.

17. A capsule as recited in claim 16 wherein said opening has a configuration and size corresponding to the cross-sectional configuration and size of the ovarian ligament.

18. A capsule as recited in claim 16 wherein said opening has a configuration and a size smaller than the cross-sectional configuration and size of the ovarian ligament.

19. A capsule as recited in claim 18 wherein said opening is expandable and contractible.

20. A capsule as recited in claim 10 and further including engaging members on said capsule body for engagement by an instrument used to move said capsule body between said open and closed positions.

21. A capsule as recited in claim 20 wherein said engaging members are disposed on said first and second portions, respectively.

22. A capsule as recited in claim 10 and further including a drain extending from said capsule body and having a passage communicating with said interior and an open end for being disposed at a drainage site in the patients body whereby substances within said interior are released at the drainage site through said open end.

23. A capsule as recited in claim 22 wherein said drain extends from one of said first and second portions.

24. A capsule as recited in claim 23 wherein said drain includes a tubular member extending from one of said first and second portions.

25. A capsule as recited in claim 24 wherein said tubular member is made of soft material atraumatic to anatomical tissue.

26. A capsule for encapsulating an ovary in the body of a patient comprising
   a hollow capsule body enclosing an interior
   an opening in said capsule body communicating with said interior for receiving an ovarian ligament to extend therethrough to position the ovary carried by the ovarian ligament in said interior for encapsulation by said capsule body; and
   a drainage channel extending from said capsule body and having a first end communicating with said interior and an open, second end spaced from said first end for draining substances from said interior.

27. A capsule as recited in claim 26 wherein said drainage channel includes a tubular member extending from said capsule body.

28. A capsule as recited in claim 27 wherein said tubular member has a length between said first and second end for positioning of said second end at a selected drainage site in the patient's body.

29. A capsule as recited in claim 28 wherein said tubular member is made of a soft material atraumatic to anatomical tissue.

30. A capsule for encapsulating both ovaries in the body of patient comprising
   a capsule body enclosing an interior for receiving both ovaries of a patient, said capsule body being manually movable between an open position wherein a space is formed in said capsule body communicating with said interior allowing both ovaries of the patient to be introduced in said interior through said space and a closed position wherein said space is contracted to prevent withdrawal of the ovaries from said interior, and at least one opening in said capsule body communicating with said interior for receiving the ovarian ligaments of the ovaries whereby the ovarian ligaments pass through said at least one opening with the ovaries encapsulated by said capsule body.

31. A method of encapsulating an ovary in the body of a patient comprising the steps of
   introducing an ovarian capsule in the abdominal cavity of the patient;
   opening the capsule to provide access to the interior of the capsule;
   positioning an ovary of the patient in the interior of the capsule; and
   closing the capsule to prevent withdrawal of the ovary from the interior whereby the ovary is encapsulated by the ovarian capsule.

32. A method of encapsulating an ovary as recited in claim 31 wherein said step of introducing includes introducing the ovarian capsule in the abdominal cavity through a small size port in the abdominal cavity wall.

33. A method of encapsulating an ovary as recited in claim 32 and further including, prior to said step of introducing, the steps of introducing a distal end of a remote visualization device in the abdominal cavity through a small size port in the abdominal cavity wall and visualizing the abdominal cavity with the remote visualization device from externally of the abdominal cavity wall.

34. A method of encapsulating an ovary as recited in claim 33 wherein said steps of opening and closing the ovarian capsule include the steps of opening and closing the ovarian capsule from externally of the abdominal cavity wall.

35. A method of encapsulating an ovary as recited in claim 34 wherein said steps of opening and closing the ovarian capsule include the steps of engaging the ovarian capsule with a distal end of an instrument extending through a small size port in the abdominal cavity wall and operating the instrument from externally of the abdominal cavity wall to open and close the ovarian capsule.

36. A method of encapsulating an ovary as recited in claim 35 wherein the instrument is a forceps and said step of introducing the ovarian capsule includes introducing the distal end of the forceps in the abdominal cavity with the ovarian capsule carried by the distal end of the forceps.

37. A method of encapsulating an ovary as recited in claim 36 and further including, subsequent to said step of closing, the steps of withdrawing the distal end of the forceps from the abdominal cavity and leaving the ovarian capsule in the abdominal cavity to encapsulate the ovary.

38. A method of encapsulating an ovary as recited in claim 37 wherein said step of leaving includes preventing fertilization of ova released by encapsulated ovary.

39. A method of encapsulating an ovary as recited in claim 38 and further including, subsequent to said step of leaving, the step of draining substances from the interior of the ovarian capsule.

40. A method of encapsulating an ovary as recited in claim 39 wherein said step of draining includes draining fluid from the interior into an anatomical space isolated from the anatomical cavity.

41. A method of encapsulating an ovary as recited in claim 40 wherein said step of draining includes draining fluid from the interior into a retroperitoneal space.

42. A method of encapsulating an ovary as recited in claim 40 wherein a tubular member extends from the ovarian capsule and has a first end attached to the ovarian capsule in communication with the interior and has an open, free end and said step of draining includes burying the open, free end of the tubular member in an anatomical space isolated from the abdominal cavity.

43. A method of encapsulating an ovary as recited in claim 36 wherein said step of engaging includes engaging members of the ovarian capsule with the distal end of the forceps.

44. A method of encapsulating an ovary as recited in claim 31 wherein said step of positioning includes grasping the ovary with a distal end of an instrument extending through a small size port in the abdominal cavity wall.

45. A method of encapsulating an ovary in the body of a patient comprising the steps of introducing an ovarian capsule in the abdominal cavity of the patient;

moving first and second portions of the ovarian capsule away from one another to create a space in the ovarian capsule communicating with an interior of the ovarian capsule;

positioning an ovary of the patient through the space and into the interior of the capsule; and moving the first and second portions of the ovarian capsule toward one another to close the space and encapsulate the ovary.

46. A method of encapsulating an ovary as recited in claim 45 wherein said steps of moving include pivoting the first and second portions.

47. A method of encapsulating an ovary as recited in claim 46 wherein the first and second portions are connected to one another by a connecting segment, and said steps of moving include pivoting the first and second portions about the connecting segment.

48. A method of encapsulating an ovary as recited in claim 47 wherein said steps of moving include moving the first and second portion with a distal end of a instrument introduced in the abdominal cavity.

49. A method of encapsulating an ovary as recited in claim 48 wherein the first and second portions are biased toward one another, said step of moving the first and second portions away from one another includes moving the first and second portions in opposition to the bias.

50. A method of encapsulating an ovary as recited in claim 49 wherein said step of moving the first and second portions toward one another includes moving the first and second portions with the force of the bias.

51. A method of encapsulating an ovary as recited in claim 48 and further including, prior to said steps of moving, the step of engaging the distal end of the instrument with engaging members on the first and second portions, respectively.

52. A method of encapsulating an ovary as recited in claim 51 wherein said step of engaging includes engaging grasping members at the distal end of the instrument with the engaging members, respectively.

53. A method of encapsulating an ovary as recited in claim 45 wherein said step of positioning includes positioning the ovarian ligament of the ovary to extend through an opening in the ovarian capsule.

54. A method of encapsulating an ovary as recited in claim 45 wherein said step of positioning includes positioning both ovaries of the patient in the interior and said step of moving the first and second portions toward one another includes encapsulating both ovaries in the ovarian capsule.

* * * * *